(12) United States Patent
Lundholt et al.

(10) Patent No.: US 8,506,542 B2
(45) Date of Patent: Aug. 13, 2013

(54) TWO-PIECE OSTOMY DEVICE WITH GUIDING AID FOR COUPLING

(75) Inventors: Rasmus Lundholt, Copenhagen S (DK); Anders Rørdam Michelsen, Viby Sjaelland (DK); Philip Olsen, Ishoej (DK); Lars Olav Schertiger, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/388,669

(22) PCT Filed: Aug. 4, 2010

(86) PCT No.: PCT/DK2010/050202
§ 371 (c)(1),
(2), (4) Date: May 10, 2012

(87) PCT Pub. No.: WO2011/015201
PCT Pub. Date: Feb. 10, 2011

(65) Prior Publication Data
US 2012/0220966 A1     Aug. 30, 2012

(30) Foreign Application Priority Data

Aug. 4, 2009  (DK) ................................ 2009 70077

(51) Int. Cl.
*A61F 5/44*      (2006.01)
*A61M 1/00*     (2006.01)
*A61B 19/00*    (2006.01)

(52) U.S. Cl.
USPC ........... 604/342; 604/317; 604/326; 604/327; 604/332; 604/337; 604/344; 604/356

(58) Field of Classification Search
USPC .................................................. 604/317–357
See application file for complete search history.

(56) References Cited

U.S. PATENT DOCUMENTS

| | | | |
|---|---|---|---|
| 3,736,934 A | 6/1973 | Hennessy | |
| 4,359,051 A | 11/1982 | Oczkowski | |
| 5,139,492 A | 8/1992 | Leise, Jr. et al. | |
| 5,356,399 A | 10/1994 | Takahashi | |
| 5,520,670 A | 5/1996 | Blum | |
| 5,662,629 A | 9/1997 | Steer et al. | |
| 5,947,941 A | 9/1999 | Leise, Jr. et al. | |
| 2007/0005032 A1 | 1/2007 | Shan et al. | |

FOREIGN PATENT DOCUMENTS

| | | |
|---|---|---|
| DE | 4203950 | 8/1992 |
| DE | 29915282 | 1/2000 |
| EP | 0598625 | 5/1994 |

OTHER PUBLICATIONS

Office Action mailed on in US Serial No.

*Primary Examiner* — Jacqueline Stephens
*Assistant Examiner* — Andrew J Mensh
(74) *Attorney, Agent, or Firm* — Coloplast Corp., Coloplast A/S; Nick Baumann (57) ABSTRACT

The invention relates to a two-piece ostomy device comprising a base plate for adhering to the skin surrounding a stoma and a releasable collecting bag for collecting output from said stoma. The base plate is releasably connectable to the collecting bag via a first annular flange arranged on the base plate and a second annular flange arranged on the collecting bag. An adhesive is at least partly disposed on at least one of the flanges. The ostomy device further comprises a first through-going hole extending through the first annular flange along a first axis and a second through-going hole extending through the second annular flange along a second axis, wherein the ostomy device further comprises a guiding aid for arranging the first annular flange and the second annular flange in a guiding configuration. In the guiding configuration the movement of the first and the second flange is limited relative to each other in one plane being defined by the first and the second axis and in rotation around at least one of the first or the second axis. The limited movement of the base plate and the collecting bag provides a two-piece system which is easier to apply correctly and thus reduces the risk of leakage.

4 Claims, 6 Drawing Sheets

TWO-PIECE OSTOMY DEVICE WITH GUIDING AID FOR COUPLING

TECHNICAL FIELD

The present invention relates to a two-piece ostomy device having a guiding aid for aiding a user when coupling an ostomy collecting bag with a base plate.

BACKGROUND

Two-piece ostomy devices are ostomy products which comprise a base plate that can be adhered to the skin surrounding a stoma and an ostomy collecting bag which is replaceably attached to the base plate.

Such two-piece ostomy devices are typically used by users who desire a base plate which has a longer wear time in order to spare the skin from frequent changes.

The base plate and the ostomy bag are typically coupled together by either a so-called mechanical coupling or an adhesive coupling. Mechanical couplings are often perceived as safer solutions, i.e. they provide a better seal and are easier to couple together. In some mechanical solutions, a so-called 'click' function is incorporated which gives an audible 'click'-sound when the two parts have been successfully coupled together.

Adhesive couplings are usually formed of two flanges, one provided on the base plate and the other on the ostomy bag. The flanges are adhered together by an adhesive disposed between the flanges. Typically, the adhesive is disposed on one of the flanges. Adhesive couplings have the advantage of being more flexible and discreet than mechanical couplings. Therefore, adhesive couplings are usually not provided with the 'click'-functions as described above, as such a relatively advanced mechanical solution would compromise the flexibility of the adhesive couplings.

However, there is an increased risk with traditionally adhesive couplings for the two flanges not to be properly aligned when adhered together, which may compromise the seal of the coupling and thereby increase the risk of a leakage.

Thus, there is a need for providing an aid for guiding the two parts together in correct alignment before adhering together.

BRIEF DESCRIPTION

When describing the different parts in the following description, the terms distal and proximal will be used in order to facilitate the understanding of the intended orientation of the parts in respect to each other and the user during use. Thus, the term proximal will be used for surfaces and sections of the respective parts that face towards the user when the ostomy device has been properly applied around the stoma, and the term distal will be used for the surfaces and sections of the respective parts facing away from the user.

The invention relates to a two-piece ostomy device comprising a base plate for adhering to the skin surrounding a stoma and a releasable collecting bag for collecting output from said stoma, wherein the base plate is releasably connectable to the collecting bag via a first annular flange arranged on the base plate and a second annular flange arranged on the collecting bag, and where an adhesive is at least partly disposed on at least one of the flanges, the ostomy device further comprises a first through-going hole extending through the first annular flange along a first axis and a second through-going hole extending through the second annular flange along a second axis, wherein the ostomy device further comprises a guiding aid for arranging the first annular flange and the second annular flange in a guiding configuration where the movement of the first and the second flange is limited relative to each other in one plane being defined by the first and the second axis and in rotation around at least one of the first or the second axis.

The limited movement of the base plate and the collecting bag provides a two-piece system which is easier to apply correctly and thus reduces the risk of leakage.

Moreover, seeing that it is possible to still rotate the base plate or/and the collecting bag around their respective axes, it is possible to place the parts in a suitable position relative to each other and thereby provide a more comfortable ostomy device which fits the individual curvature of the body. In some cases, this may even prevent the ostomy device from unintentionally coming lose as some positions may result in the body exerting a high load on the device causing it to disengage.

It should be understood that the guiding aid may be formed as a set of parts arranged on different parts of the ostomy device, e.g. the base plate and the collecting bag. However, the guiding aid may also be a separate unit altogether. Examples of this will be given herein. Thus, the term guiding aid should not be interpreted limiting to only one part or piece but is also able to encompass a set of parts which together function as a guiding aid as defined by the claims.

Such a guiding aid is of particular use in two-piece ostomy devices wherein the first annular flange is attached to the base plate via a first annular attachment zone from which a first free outer flange section extends in a radial direction away from the first axis and the second annular flange is attached to the collecting bag via a second annular attachment zone from which a second free outer flange section extends in a radial direction away from the second axis, as these device may be difficult to align correctly as they tend to be very flexible.

In one embodiment of a two-piece ostomy device, the guiding aid comprises a sheet with an at least partly annular cut-out having a radius equal to or larger than the radial distance from the second axis to the outer edge of the second annular attachment zone, a guiding tab extending in a radial direction away from the centre of the annular cut-out and a recess arranged on the first annular flange having dimensions capable of receiving the guiding tab. This provides an ostomy device which has a guiding aid that is clearly and easily identifiable by the user by touch.

During attachment of the collecting bag, the sheet may function as a stabilizing layer, thereby facilitating coupling. Different materials and dimensions may thus be chosen for the sheet, depending on the desired stiffness, flexibility or other characteristics suitable for the sheet.

However, seeing that most users who use an adhesive two-piece ostomy device have a desire for it to be discreet and flexible, it is desirable that the sheet may be easily removed after the base plate and the collecting bag have been coupled together. Thus, in one embodiment, the sheet is perforated along its axis of symmetry, which allows the sheet to be easily removed and discarded.

In order to prevent the sheet from getting stuck in the recess due to an excess of material when the sheet is removed, the guiding tab may be provided with a further cut-out.

In one embodiment, the recess may be defined by the first annular flange, a first and a second tab extending axially from the first annular flange and a bridge part connecting the ends of the first and second tab.

In another embodiment of the two-piece ostomy device, the guiding aid comprises a sheet formed with a first and a second at least partly annular cut-out, wherein the first cut-out has a radius equal to or larger than the radial distance from the first axis to the outer edge of the first annular attachment zone, and the second cut-out has a radius equal to or larger than the radial distance from the second axis to the outer edge of the first annular attachment zone. This provides an easy to handle guiding aid, which may be easily discarded. Furthermore, such guiding aid may easily be introduced to the current production of two-piece adhesive ostomy devices as it does not necessitate any alterations to the base plate or collecting bag of many known devices.

Advantageously, the two-piece ostomy device may be formed so that the distance between the centre of the first cut-out and the second cut-out is equal to or larger than the radial distance from the first axis to the outer edge of the first flange and the radial distance from the second axis to the outer edge of the second flange. This prevents the first and the second annular flange from being unintentionally bent and the guiding aid from unintentionally falling off.

As described previously above, the sheet may be provided with a perforation line dividing the sheet along a line through the centre of the first cut-out and the centre of the second cut-out, so that the sheet is easily removed.

At least two handling tabs may be protruding from the sheet on opposite sides of the perforation line. This provides handling areas so that the user can easily grab a hold off and manipulate the sheet.

The second cut-out may be fully annularly arranged in the sheet. This allows for the sheet to be arranged on the collecting bag during manufacturing in such a way that it is difficult to pull off without tearing the sheet or the collecting bag.

In yet another embodiment of the two-piece ostomy device, the guiding aid comprises a receiving slot arranged on the base plate or the ostomy bag facing the same direction as the respective annular flange, wherein the slot extends in a radial direction from the respective first or second axis and has a radial curvature corresponding to that of the opposing annular flange.

After use of the guiding aid, the receiving slot is no longer needed. Thus, the receiving slot may be detachably arranged on the ostomy bag, so that it may be discarded after use in order to prevent it from irritating the skin or getting caught in e.g. clothing or the like.

BRIEF DESCRIPTION OF THE DRAWINGS

FIG. 2-6a shows the application of the first embodiment of a two-piece ostomy device, FIG. 8-14 shows the application of the second embodiment of a two-piece ostomy device, FIG. 16-20 shows the application of the third embodiment of a two-piece ostomy device.

DETAILED DESCRIPTION

Figure 1:
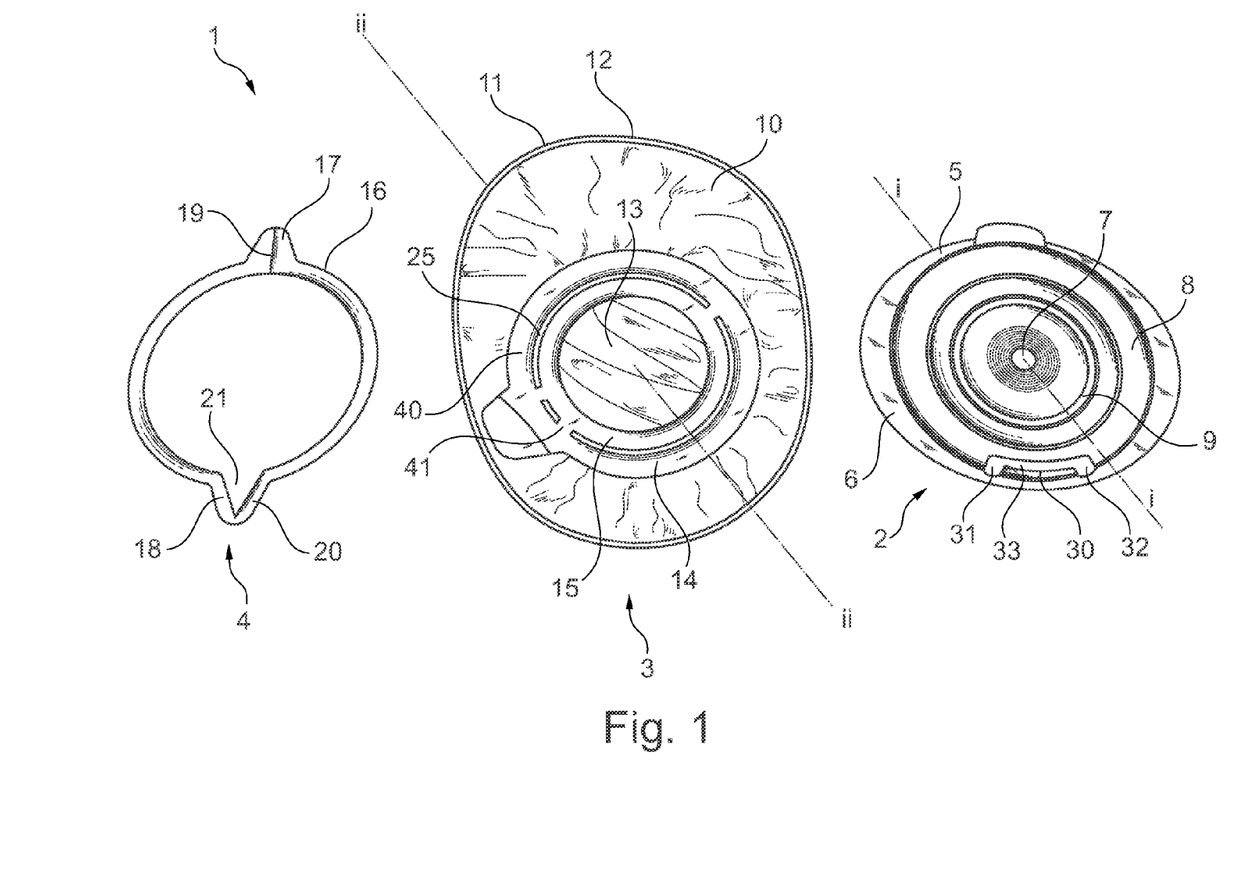
FIG. 1 shows the components of a first embodiment of the two-piece ostomy device.

The different elements of a first embodiment of an ostomy device 1 are shown in FIG. 1.

The ostomy device is formed of a base plate 2, a collecting bag 3 and a guide ring 4.

The basic construction of the base plate and the collecting bag is similar to that of known base plates and collecting bags for use in adhesive two-piece ostomy devices, such as the base plates and collecting bags for use in the Easiflex product line which is marketed by Coloplast A/S. In the following description, such known parts will form the basis for illustrating and describing the different embodiments. Thus, for the known and similar parts like reference numbers will be used for the different embodiments in order to facilitate reading and understanding.

The base plate is adapted to be attached to the skin around a stoma and is capable of coupling with the collecting bag so that output from the stoma is received in the bag. The base plate comprises a skin friendly adhesive layer 5, which has been disposed on the proximal side of a backing layer 6. A first through-going hole 7 is provided in the adhesive layer and the backing layer. On the distal side of the backing layer, a first annular flange 8 is attached to the backing layer along a first annular weld 9 extending around the through-going hole 7.

The adhesive layer 5, the first through-going hole 7 and the first annular flange 8 are arranged coaxially along a central axis of the base plate.

The adhesive layer 5 provides an adhesive proximal surface suitable for adhering to the skin. The backing layer 6 is particularly advantageous during production as it serves as a guide layer for aligning the adhesive correctly and as a welding base for welding the first annular flange 8 thereto. Moreover, the backing layer serves as a protective cover during use so that the adhesive only adheres to the skin and not to unwanted articles such as clothes or the collecting bag.

The collecting bag 3 is formed of a first and a second foil sheet 10, 11, which at their periphery are welded together along the weld 12.

A second through-going hole 13 is provided in the first foil sheet 10 and a second annular flange 14 is attached to the proximal side of the first foil sheet along a second annular weld 15 extending around the second through-going hole 13.

On the proximal surface of the second annular flange 14, a second adhesive layer 40 is disposed, which is suitable for providing an adhesive connection between the first annular flange 8 and the second annular flange 14, thereby providing an adhesive coupling between the base plate and the collecting bag. During storage, the second adhesive layer is covered by a release liner 41. The release liner is removed prior to use of the collecting bag, thereby exposing the second adhesive layer.

The second through-going hole 13 and the annular flange 14 are arranged coaxially along a central axis of the collecting bag.

The base plate and collecting bag as described above are very similar to parts used in adhesive two-piece ostomy devices, such as the Easiflex product line mentioned previously.

The illustrated base plate construction mainly differs from known adhesive base plates in that, at the periphery of the first annular flange 8, a guide slot 30 is provided which extends in an axial direction from the first annular flange. The guide slot is defined by the distal surface of the annular flange 8, a first and second spacer 31, 32 extending axially from the distal surface of the annular flange 8 and being placed along the periphery of the first annular flange and a bridging element 33 connecting the first and the second spacer.

The guide ring 4 is formed as an annular ring 16 defined by an inner circumference 16' and an outer circumference 16". The guide ring further has a first tab 17 extending in a radial direction from the annular ring and a second tab 18 extending opposite the first tab in a direction radially away from the annular ring.

A first tear line 19 extending in a radial direction from the centre of the annular ring is provided in the first tab 17, dividing the first tab 17 into symmetrical halves.

A second tear line 20 extending in a radial direction from the centre of the annular ring is provided in the second tab 18, dividing the second tab 18 into symmetrical halves.

The second tab is provided with a recess 21 arranged as a cut-out extending radially inwards from the second tab 18.

The inner circumference 16' of the annular ring 16 is slightly larger than the outer circumference 15" of the second annular weld 15. This enables the guide ring 4 to be rotatably arranged on the collecting bag 3 along the central axis of the collecting bag. This prevents the guide ring 4 from falling off as it may be arranged so that it is retained by the groove 25 defined by the outer circumference 15" of the second annular weld, the proximal surface of the first foil sheet 10 and the distal surface of the second annular flange 14.

The guide ring 4 may be formed of any suitable sheet material having a desired stiffness. Such materials could be a thermoformed hard polymer foil, punched coated cardboard, thermoformed composite materials or injection moulded polymers.

In the following, it will be described how the first embodiment of the ostomy device is used, with reference to FIGS. 2-7.

Figure 2:
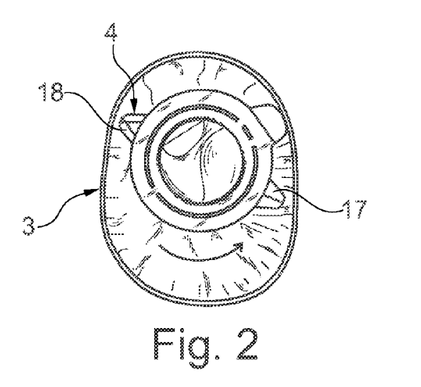

First the guide ring is rotated as shown by the arrow in FIG. 2 so that the second tab 18 is in a suitable position, as will be explained below.

Figure 3:
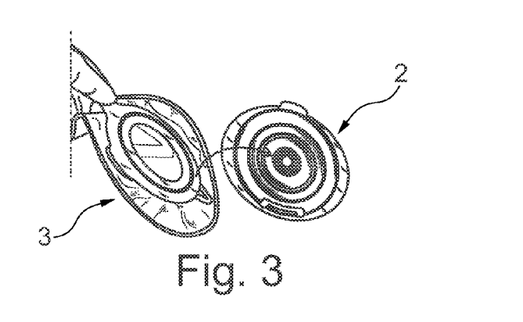

Then, as illustrated in FIG. 3, the second tab is arranged in the guide slot 30 of the base plate 2 which is arranged on the skin surrounding the stoma so that the stoma extends through the first through-going hole 7. Seeing that the tab has previously been rotated to a suitable position, the collecting bag will align with the base plate in a desired position relative to the base plate and the stoma.

Figure 4:
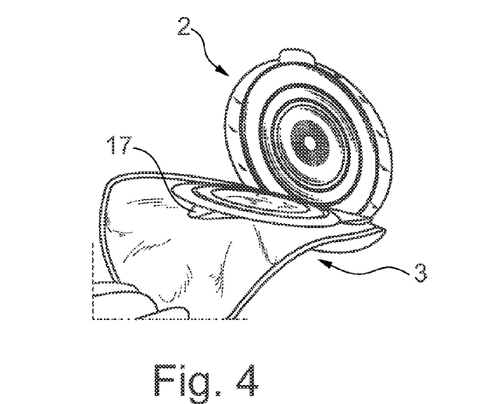

As shown in FIG. 4, the base plate and the ostomy collecting bag are now arranged in a suitable position relative to each other. As can be understood, the relative movement of the central axis of the base plate in respect to the central axis of the collecting bag is now limited to one plane defined by the two axes.

However, due to the rotatable relationship between the guide ring and the collecting bag, the collecting bag may still be rotated around its central axis. This allows the user to make any final adjustments before removing the release liner and coupling the first and second flanges together via the second adhesive layer.

Figure 5:
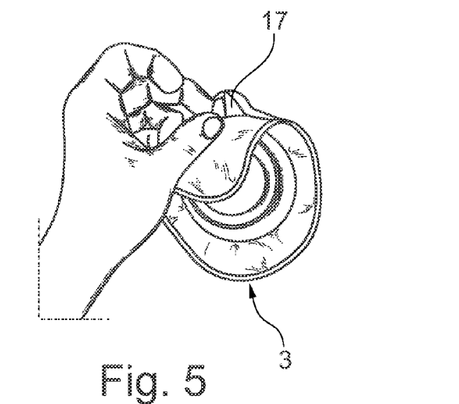
Figure 6:
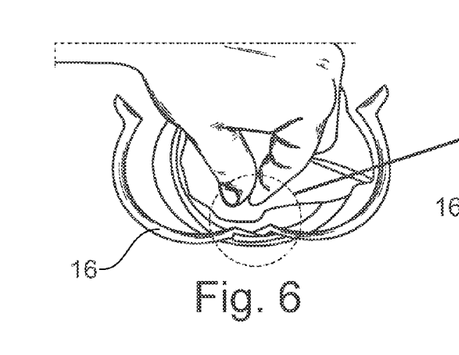
Figure 6A:
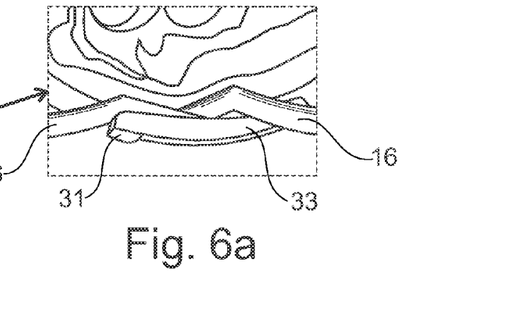

Finally, the guide ring 4 is removed by pulling on opposite sides of the tear line on the first tab, as shown in FIG. 5. This tears the guide ring, which may subsequently be discarded. As seen in FIGS. 6 and 6a, the recess in the second tab allows the guide ring to be removed from the slot.

Figure 7:
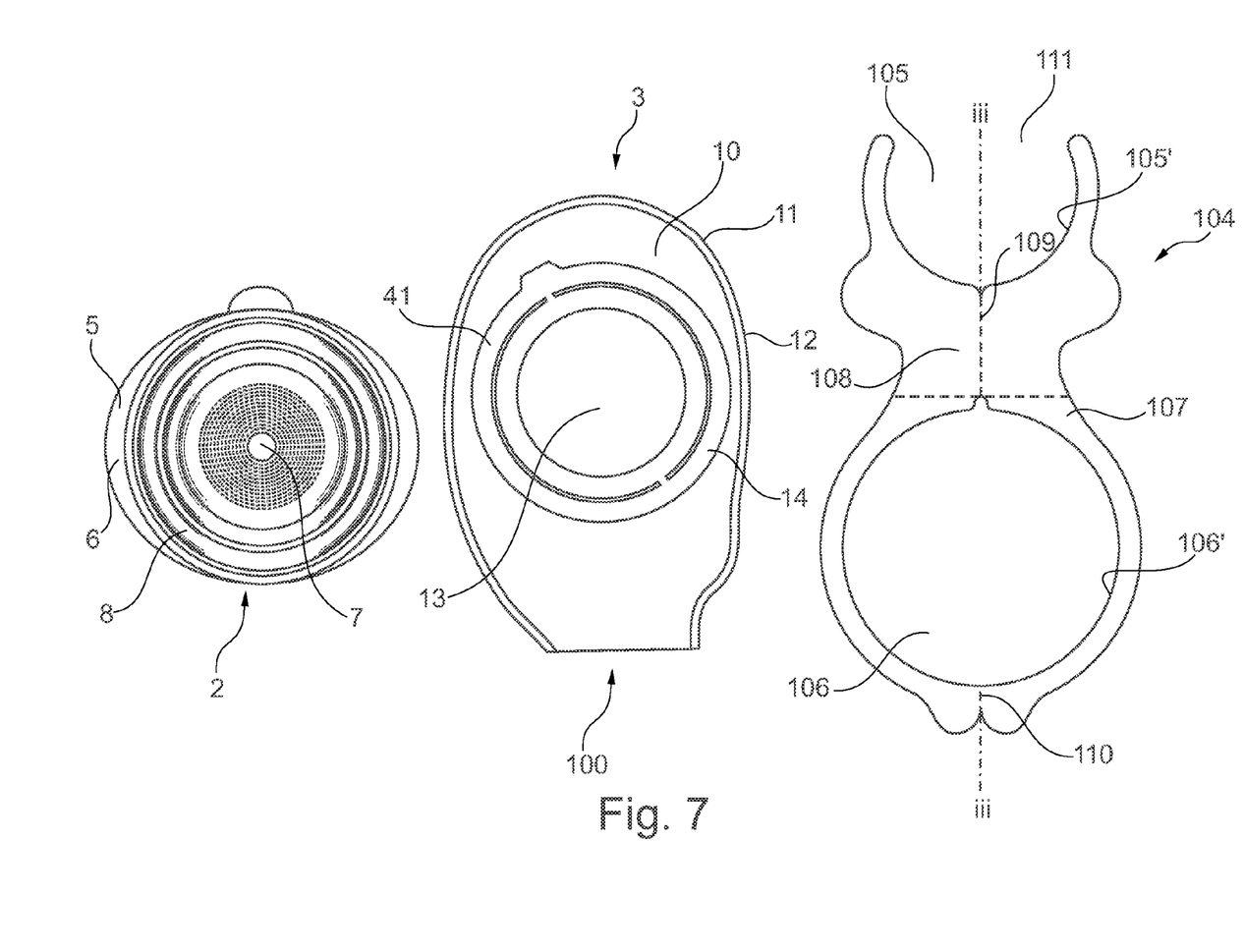
FIG. 7 shows the components of a second embodiment of a two-piece ostomy device.

The different elements of a second embodiment of an ostomy device 100 are shown in FIG. 7. The ostomy device 100 is formed of a base plate 2 and a collection bag 3. The base plate and the collection bag are similar to that of a typical adhesive two-piece ostomy device, such as the Easiflex two-piece ostomy device produced by Coloplast A/S. Such similar devices have been described above in respect to the first embodiment of an ostomy device, thus, in order to facilitate the reading, similar parts have been given the same reference numerals. In addition thereto, the ostomy device furthermore comprises a guiding aid 104.

The guiding aid is formed as a wrench-like assembly, where a first and a second annular cut-out 105, 106 is provided on a sheet 107. The cut-outs are spaced apart by a spacing section 108 of the sheet 107.

A first tear-line 109 is provided in the spacing section 108 and a second tear line 110 is provided in the sheet 107 at the second annular cut-out opposite the first tear-line. The first and the second tear-line is provided along an axis of symmetry iii-iii of the guiding aid 104.

The first cut-out 105 has a first inner circumference 105' slightly larger than the outer circumference 9" of the first annular weld 9. Furthermore, the sheet 107 does not extend around the entire first cut-out but is interrupted by an opening 111.

Figures 8, 9:
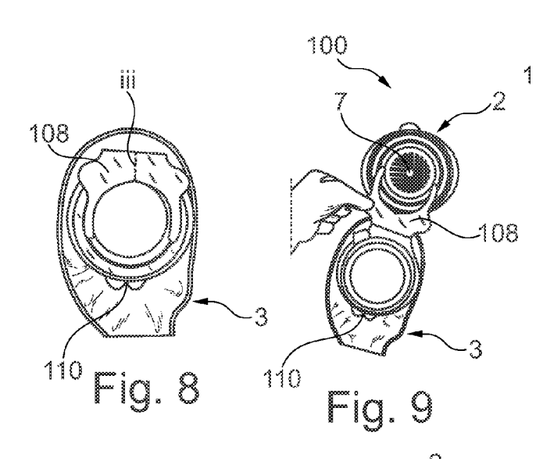

The second cut-out 106 has a second inner circumference 106' slightly larger than the outer circumference 15" of the second annular weld 15. This enables the guiding aid to be rotatably arranged on the collecting bag 3 around the central axis of the collecting bag. This prevents the guiding aid 104 from falling off as it may be arranged so that it is retained in the groove 25 defined by the outer circumference 15" of the second annular weld, the proximal surface of the first foil sheet 10 and the distal surface of the second annular flange 14, as shown in FIG. 8. The guiding aid 104 may advantageously be arranged on the collecting bag 3 during the manufacturing of the collecting bag 3.

The guiding aid 104 may be formed of any suitable sheet material having a desired stiffness. Such materials could be a thermoformed hard polymer foil, punched coated cardboard, thermoformed composite materials or injection moulded polymers.

In the following, it will be described how the second embodiment of the ostomy device is used, with reference to FIGS. 9-14.

As seen in FIG. 9, the opening 111 allows the user to arrange the first cut-out around the first annular weld. This coupling of the base plate 2 and the collecting bag 3 via the guiding aid 104 provides a limited relative movement of the base plate 2 and the collecting bag 3. As can be understood the movement of the central axis of the base plate and the central axis of the ostomy bag is limited to be within one plane defined by the two axes. However, the guiding aid allows both the base plate and the collecting bag to be rotated around their respective axes allowing the user to arrange the two parts in a suitable position.

Figure 10:
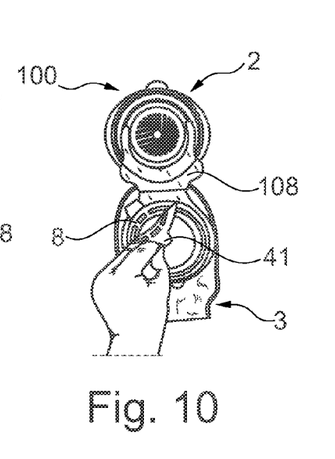
Figure 11:
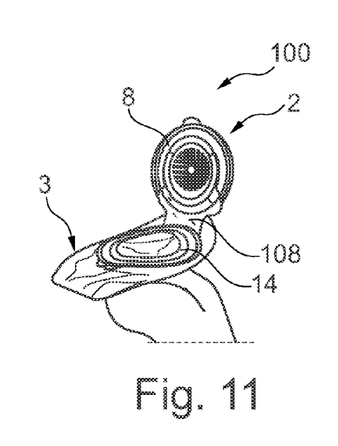
Figure 12:
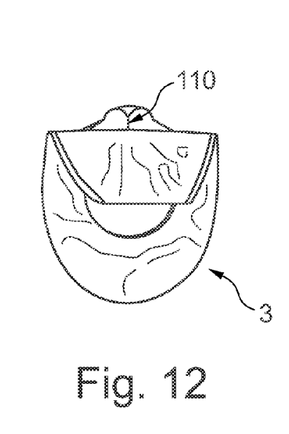

When the base plate and the collecting bag has been arranged in a suitable position, the user removes the release liner as shown in FIG. 10 and folds the ostomy bag towards the base plate as shown in FIG. 11 so that the first annular flange and the second annular flange adhere together. Now the collecting bag is properly coupled to the base plate and the ostomy device is ready for use, as shown in FIG. 12.

Figure 13:
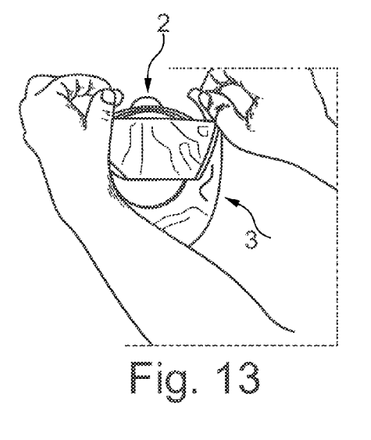
Figure 14:
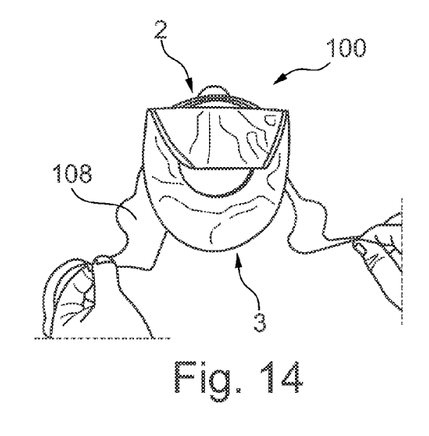

However, should the user so desire, the guiding aid 104 may be removed by tearing along the first and the second tear line 109, 110, as illustrated in FIGS. 13 and 14.

A folding line 115 may be formed across the spacing section 108. The folding line is arranged so that when the guiding aid 104 is folded around the folding line, the central axis of the base plate and the central axis of the collecting bag are co-axially aligned. Such a folding line may be pre-formed, e.g. by bending it during manufacturing, or a visual indicator, such as a printed line, may show where to fold in order to obtain correct alignment.

Figure 15:
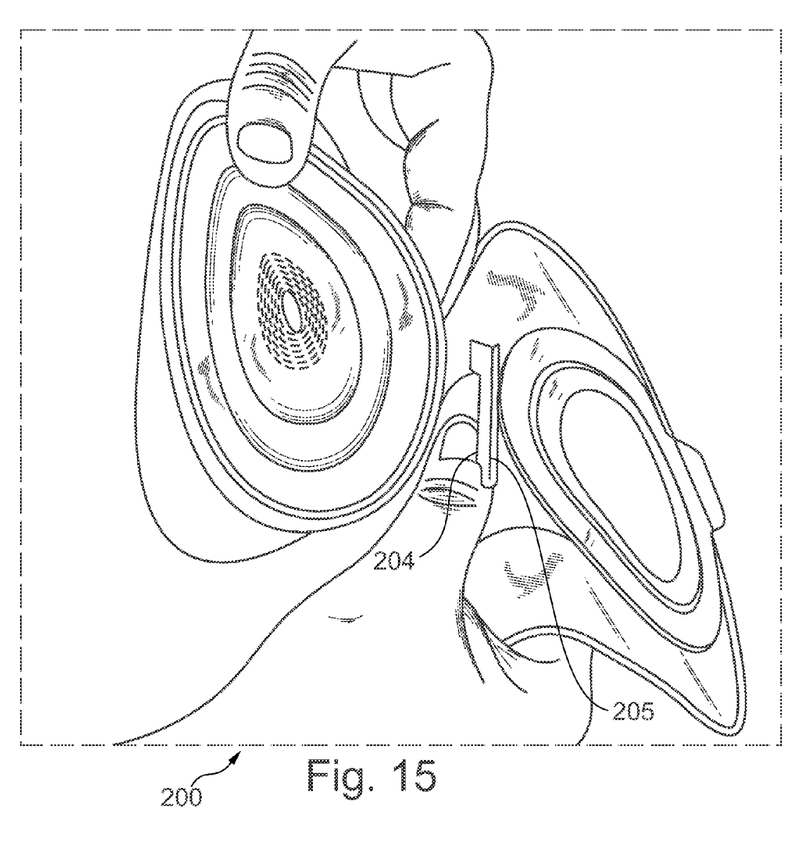
FIG. 15 shows the components of a third embodiment of a two-piece ostomy device.

The different elements of a third embodiment of an ostomy device 200 are shown in FIG. 15. The ostomy device 200 is formed of a base plate 2 and a collection bag 3. The base plate and the collection bag are similar to those of a typical adhesive two-piece ostomy device, such as the Easiflex two-piece ostomy device produced by Coloplast A/S. Such similar devices have been described above in respect to the first and the second embodiment of an ostomy device, thus, in order to facilitate the reading, similar parts have been given the same reference numerals.

In addition thereto, the ostomy device further comprises a guiding tab 204. The guiding tab 204 is arranged on the proximal side of the collecting bag. A receiving slot 205 is formed in the guiding tab 204. The slot is formed and shaped so as to receive a section of the edge of the first annular flange 8., i.e., seen in a radial direction from the centre axis of the collecting bag, the slot begins at a distance less than the radial extent of the first annular flange and the slot extends in a radial direction away from the central axis of the collecting bag at a distance slightly larger than the radial extent of the first annular flange. The slot further has a thickness, i.e. an axial extent along the central axis of the collecting bag, slightly larger than the thickness of the first annular flange. The slot ends in a curved shape corresponding to the curvature of the first annular flange.

The guiding tab 204 is releasably attached to the collecting bag. This may for example be done with a velcro coupling or a snap lock. Thus, after the guiding tab has been used it may be discarded.

In the following, it will be described how the third embodiment of the ostomy device is used, with reference to FIGS. 16-20.

Figure 16:
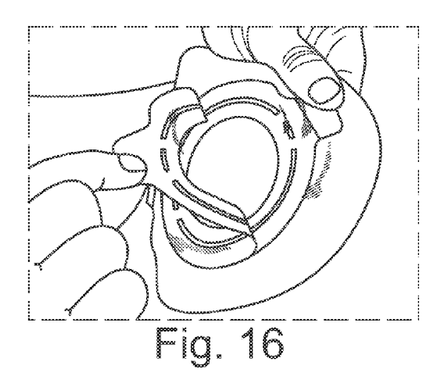
Figure 17:
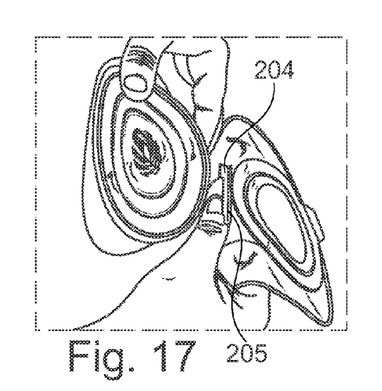
Figure 18:
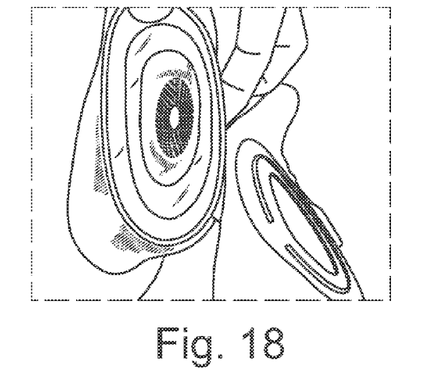
Figure 19:
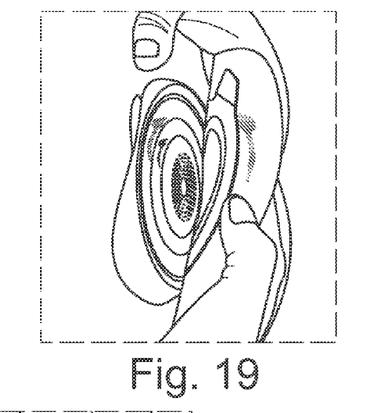

First, the release liner is removed from the second annular flange on the collecting bag as shown in FIG. 16. Then, the guiding tab is aligned with the first annular flange, as seen in FIG. 17. After this, the guiding tab and the first annular flange are coupled together, i.e. the first annular flange is received in the slot, as shown in FIG. 18. In this position, the central axis of the base plate and the central axis of the collecting bag are relatively fixed in relation to each other so that the axes are only movable in one plane defined by them. However, the guide tab is able to slide along the edge of the first annular flange, thus enabling rotation of the collecting bag around the central axis thereof. This allows the user to rotate the collecting bag into a suitable position before adhering the first and the second annular flange together, as seen in FIG. 19.

Alternatively the removal of the release liner, as shown in FIG. 16, may be delayed until the guide tab has coupled with the first annular flange, as shown in FIG. 18.

Figure 20:
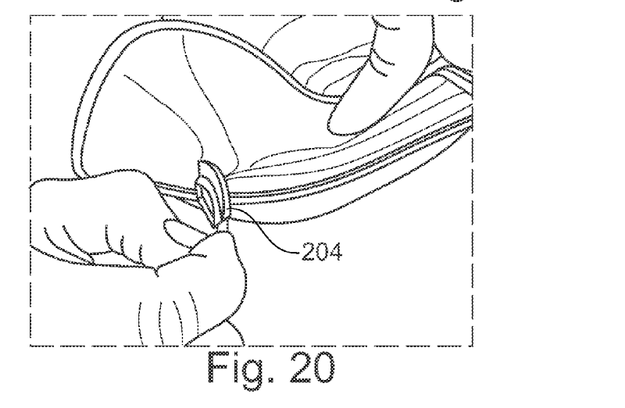

Finally, the guide tab may be removed as shown in FIG. 20. Thus, the guide tab will not be present during use where it could be in the way, for example by rubbing against the skin causing itching or cuts or getting caught in clothing.

Although not shown, the edge of the first annular flange may be provided with a rim having an increased thickness larger than the adjacent flange material. The receiving slot may be provided with a similar complementary groove. This provides a 'click'-coupling where engagement is improved but the rotating relation between the collecting bag and the base plate is maintained.

With respect to the embodiments above, some dimensions have been referred to as being slightly larger than other dimensions. Such a slightly larger dimension is of course relative and is modified based on the desired fit. Thus, if a tight fit is desired, the slightly larger dimension should be almost equal to the other dimension. However, if a more loose fit is desired, maybe due to production tolerances, or since some users may be disabled and require larger dimensions to operate the ostomy device correctly, the slightly larger dimension will result in a larger gap to the other dimension. The person skilled in the art would be capable of taking such dimensioning into consideration and he will have no problem understanding what is meant by such slightly larger dimension.

Embodiments

1. A two-piece ostomy device, comprising a base plate for adhering to the skin surrounding a stoma, and a releasable collecting bag for collecting output from said stoma, wherein the base plate is releasably connectable to the collecting bag via a first annular flange arranged on the base plate and a second annular flange arranged on the collecting bag and where an adhesive is at least partly disposed on at least one of the flanges, the ostomy device further comprising
    a first through-going hole extending through the first annular flange along a first axis, and
    a second through-going hole extending through the second annular flange along a second axis,
    wherein the ostomy device further comprises a guiding aid for arranging the first annular flange and the second annular flange in a guiding configuration where the movement of the first and the second flange is limited relative to each other
    in one plane being defined by the first and second axis, and
    in rotation around at least one of the first or the second axis.
2. A two-piece ostomy device according to embodiment 1, wherein the first annular flange is attached to the base plate via a first annular attachment zone from which a first free outer flange section extends in a radial direction away from the first axis, and the second annular flange is attached to the collecting bag via a second annular attachment zone from which a second free outer flange section extends in a radial direction away from the second axis.
3. A two-piece ostomy device according to embodiment 2, wherein the guiding aid comprises a sheet formed with a first and a second at least partly annular cut-out, wherein the first cut-out has a radius equal to or larger than the radial distance from the first axis to the outer edge of the first annular attachment zone, and the second cut-out has a radius equal to or larger than the radial distance from the second axis to the outer edge of the first annular attachment zone.
4. A two-piece ostomy device according to embodiment 3, wherein the distance between the centre of the first cut-out and the second cut-out is equal to or larger than the radial distance from the first axis to the outer edge of the first flange and the radial distance from the second axis to the outer edge of the second flange.
5. A two-piece ostomy device according to embodiment 3 or 4, wherein the sheet is provided with a perforation line dividing the sheet along a line through the centre of the first cut-out and the centre of the second cut-out.
6. A two-piece ostomy device according to embodiment 3, 4 or 5, wherein at least two handling tabs protrude from the sheet on opposite sides of the perforation line.
7. A two-piece ostomy device according to embodiment 3, 4, 5 or 6, wherein the second cut-out is fully annularly arranged in the sheet.
8. A two-piece ostomy device according to embodiment 2, wherein the guiding aid comprises a receiving slot arranged on the base plate or the ostomy bag facing the same direction as the respective annular flange, wherein the slot extends in a radial direction from the respective first or second axis and has a radial curvature corresponding to that of the opposing annular flange.
9. A two-piece ostomy device according to embodiment 8, wherein the receiving slot is detachably arranged on the ostomy bag.

REFERENCE NUMBERS

1. first embodiment of an ostomy device
2. base plate 3. collecting bag
4. guide ring
5. skin friendly adhesive layer
6. proximal side of a backing layer
7. first through-going hole
8. first annular flange
9. first annular weld
10. first foil sheet
11. second foil sheet
12. weld
13. second through-going hole
14. second annular flange
15. second annular weld
16. annular ring
17. first tab
18. second tab
19. first tear line
20. second tear line
21. recess
25. groove
30. guide slot
31. first spacer
32. second spacer
33. bridging element
40. second adhesive layer
41. release liner
100. second embodiment of an ostomy device
104. guiding aid
105. first annular cut-out
106. second annular cut-out
107. sheet
108. spacing section
109. first tear-line
110. second tear line
111. opening
200. third embodiment of an ostomy device
204. guiding tab
205. receiving slot

The invention claimed is:

1. A two-piece ostomy device, comprising a base plate for adhering to skin surrounding a stoma and a releasable collecting bag for collecting output from said stoma, wherein the base plate is releasably connectable to the collecting bag via a first annular flange arranged on the base plate and a second annular flange arranged on the collecting bag and where an adhesive is disposed on at least one of the flanges, the ostomy device further comprising:
a first through-going hole extending through the first annular flange along a first axis, and
a second through-going hole extending through the second annular flange along a second axis,
where the first annular flange is attached to the base plate via a first annular attachment zone from which a first free outer flange section extends in a radial direction away from the first axis, and the second annular flange is attached to the collecting bag via a second annular attachment zone from which a second free outer flange section extends in a radial direction away from the second axis, and where the ostomy device further comprises:
a guiding aid for arranging the first annular flange and the second annular flange in a guiding configuration where the movement of the first and the second flange is limited relative to each other
in one plane being defined by the first and second axis, and
in rotation around at least one of the first or the second axis,
wherein the guiding aid comprises:
a sheet with an annular cut-out having a radius equal to or larger than the radial distance from the second axis to the outer edge of the second annular attachment zone, said sheet having a guiding tab extending in a radial direction away from a center of the annular cut-out, and
a recess arranged on the first annular flange having dimensions capable of receiving the guiding tab.

2. A two-piece ostomy device according to claim 1, wherein the sheet is perforated along its axis of symmetry.

3. A two-piece ostomy device according to claim 1, wherein the guiding tab is provided with a further cut-out.

4. A two-piece ostomy device according to claim 1, wherein the recess is defined by the first annular flange, a first and a second tab extending axially from the first annular flange and a bridge part connecting the ends of the first and second tab.

* * * * *